(12) United States Patent
Singh et al.

(10) Patent No.: US 7,071,226 B1
(45) Date of Patent: Jul. 4, 2006

(54) AMINO-FUNCTIONALIZED 1,2,4-TRIOXANES USEFUL AS ANTIMALARIAL AGENTS AND PROCESS FOR PREPARATION THEREOF

(75) Inventors: Chndan Singh, Uttar Pradesh (IN); Heetika Malik, Uttar Pradesh (IN); Sunil Kumar Puri, Uttar Pradesh (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 11/023,905

(22) Filed: Dec. 28, 2004

(51) Int. Cl.
*A61K 31/357* (2006.01)
*C07D 323/04* (2006.01)
*C07D 323/06* (2006.01)

(52) U.S. Cl. ...................... 514/452; 549/333
(58) Field of Classification Search ............... 549/333; 514/452
See application file for complete search history.

(56) References Cited

OTHER PUBLICATIONS

Singh et al, Bioorganic & Medicinal Chemistry Letters, 14(2), p. 459-462, Jan. 2004.*

* cited by examiner

*Primary Examiner*—Bernard Dentz
(74) *Attorney, Agent, or Firm*—Ostrolenk, Faber, Gerb & Soffen, LLP

(57) ABSTRACT

The present invention relates to a novel series of antimalarial amino functionalized 1,2,4-trioxane analogues of formula 4

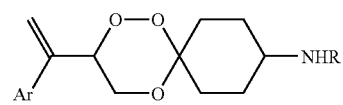

wherein Ar represents aryl groups such as phenyl, 4-biphenyl, 4-chlorophenyl, 4-methoxyphenyl, 4-methylphenyl and R represents phenyl, 4-methoxyphenyl, 4-chlorophenyl, 3,5-dichlorophenyl, 4-acetylaminophenyl, 1-naphthyl, 2-biphenyl, 4-biphenyl, 2-fluorene, 4-fluorophenyl, 2-trifluoromethylphenyl, 3-trifluoromethylphenyl and 4-trifluoromethylphenyl and the like.

14 Claims, No Drawings

AMINO-FUNCTIONALIZED 1,2,4-TRIOXANES USEFUL AS ANTIMALARIAL AGENTS AND PROCESS FOR PREPARATION THEREOF

FIELD OF THE INVENTION

The present invention relates to a novel series of antimalarial amino functionalized 1,2,4-trioxane analogues of formula 4

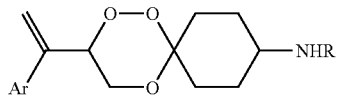

4 where Ar is an aryl group such as phenyl, 4-biphenyl, 4-chlorophenyl, 4-methoxyphenyl, 4-methylphenyl and R represents phenyl, 4-methoxyphenyl, 4-chlorophenyl, 3,5-dichlorophenyl, 4-acetylaminophenyl, 1-naphthyl, 2-biphenyl, 4-biphenyl, 2-fluorene, 4-fluorophenyl, 2-trifluoromethylphenyl, 3-trifluoromethylphenyl and 4-trifluoromethylphenyl and the like. Several of these compounds show promising antimalarial activity against multidrug-resistant malaria in mice and hold promise as antimalarial agents against multidrug-resistant malaria.

BACKGROUND OF THE INVENTION

Malaria is one of the most deadly diseases affecting third world countries, and claims more than a million lives annually. While various classes of antimalarial agents are available, chloroquine remains the main stay of therapy against malaria. Increasing resistance of *Plasmodium falciparum*, the most dangerous of the four malaria parasites that infect humans, to common drugs such as chloroquine has heightened concern about malaria. Extensive programs are underway to screen natural products and synthetic derivatives for new agents. Against this background, isolation of artemisinin as the active principle of Chinese herb *Artemisia annua* has opened new possibilities in malaria chemotherapy.

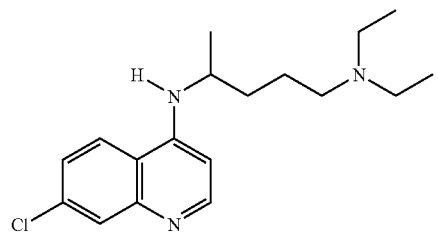

Chloroquine

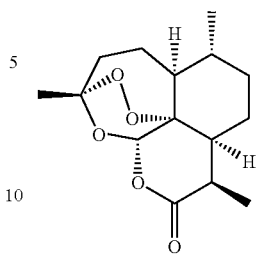

Artemisinia

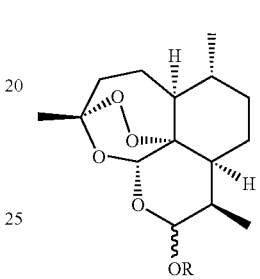

Arteether R-Et
Artemether R = Me

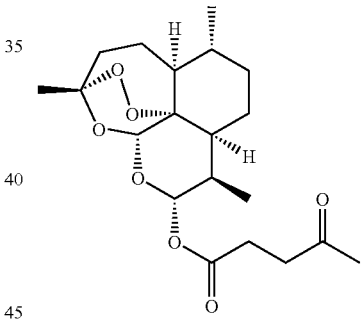

Artesunic acid

Semisynthetic derivatives of artemisinin such as arteether, artemether and artesunic acid, are currently the drugs of choice for the treatment of complicated cases of malaria such as cerebral malaria [For reviews on artemisinin and its analogues see; (a) Klayman, D. L. *Science* 1985, 228, 1049. (b) Bhattacharya, A. K.; Sharma, R. P. *Heterocycles* 1999, 51, 1681. (c) Borstnik, K.; Paik, I.; Shapiro, T. A.; Posner, G. H. *Int. J. Parasitol.* 2002, 32, 1661. (d) Ploypradith, P. *Acta Trop.* 2004, 89, 329. (e) O'Neill, P. M.; Posner, G. H. *J. Med. Chem.* 2004, 47, 2945]. The limited availability of artemisinin from natural sources and the fact that endoperoxide linkage present in form of a 1,2,4-trioxane ring system is the antimalarial pharmacophore of these compounds, has led to the present effort to develop structurally simple synthetic trioxanes. Several structurally simple synthetic 1,2,4-trioxanes have shown promising antimalarial activity [(a) Bhattacharya, A. K.; Sharma, R. P. *Heterocycles* 1999, 51, 1681. (b) Borstnik, K.; Paik, L.; Shapiro, T. A.; Posner, G. H. *Int. J. Parasitol.* 2002, 32, 1661. (c) Singh, C.; Misra, D.; Saxena, G.; Chandra, S. *Bioorg. Med. Chem. Lett.* 1995, 5, 1913. (d) Singh, C.; Puri, S. K. U.S. Pat. No. 6,316,493 B1, 2001. (e) Singh, C.; Gupta, N.; Puri, S. K. *Bioorg. Med. Chem. Lett.* 2003, 13, 3445. (f) Singh, C.; Tiwari, P.; Puri, S. K. PCT patent application No. PCT/1N02/00093, dated 28, Mar. 2002]. Singh et al. have developed a novel photooxygenation route for preparation of 1,2,4-trioxanes. β-Hydroxyhydroperoxide prepared by regiospecific photooxygenation of allylic alcohols on condensation with aldehydes or ketone in presence of acid catalyst furnish 1,2,4-trioxane. [(a) Singh, C.; Misra, D.; Saxena, G.; Chandra, S. *Bioorg. Med. Chem. Lett.* 1992, 2, 497. (b) Singh, C.; Misra, D.; Saxena, G.; Chandra, S. *Bioorg. Med. Chem. Lett.* 1995, 5, 1913. (c) Singh, C.; Puri, S. K. U.S. Pat. No. 6,316,493 B1, 2001. (d) Singh, C.; Gupta, N.; Puri, S. K. *Bioorg. Med. Chem. Lett.* 2002, 12, 1913. (e) Singh, C.; Gupta, N.; Puri, S. K. *Bioorg. Med. Chem. Lett.* 2003, 13, 3445. (f) Singh, C.; Tiwari, P.; Puri, S. K. PCT patent application No. PCT/1N02/00093 dated 28, Mar. 2002]. This method has been extended to prepare several amino functionalized 1,2,4-trioxanes, some of which have shown moderate antimalarial activity against multidrug resistant *P. yoelii* in mice [Singh, C.; Malik, H.; Puri, S. K. *Bioorg. Med. Chem. Lett.* 2004, 14, 459]. It is desirable to develop new compounds with show high degrees of anti-malarial activity in order to overcome the problems associated with the prior art compounds including the problem of drug-resistance in the malarial virus.

OBJECTS OF THE INVENTION

The main objective of the present invention is to provide novel amino functionalized 1,2,4-trioxanes with a potential to be used for the treatment of malaria.

It is another object of the invention to provide a process for the preparation of novel amino functionalized 1,2,4-trioxanes of formula 4, a new series of antimalarial agents.

SUMMARY OF THE INVENTION

The present invention provides substituted amino functionalized 1,2,4-trioxanes of formula 4

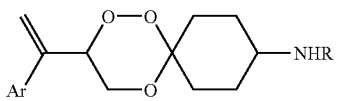

wherein Ar represents aryl groups selected from the groups consisting of phenyl, 4-biphenyl, 4-chlorophenyl, 4-methoxyphenyl and 4-methylphenyl and R represents phenyl, 4-methoxyphenyl, 4-chlorophenyl, 3,5-dichlorophenyl, 4-acetylaminophenyl, 1-naphthyl, 2-biphenyl, 4-biphenyl, 2-fluorene, 4-fluorophenyl, 2-trifluoromethylphenyl, 3-trifluoromethylphenyl and 4-trifluoromethylphenyl and the like.

In one embodiment of the invention, the compound of formula 4 has structural formula 4aa–4ai shown below:

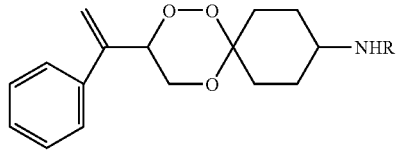

4aa R = 4-chlorophenyl
4ab R = 2-biphenyl (upper $R_f$)
4ac R = 2-biphenyl (lower $R_f$)
4ad R = 4-biphenyl
4ae R = 2-fluorene
4af R = 4-fluorophenyl
4ag R = 2-trifluoromethylphenyl
4ah R = 3-trifluoromethylphenyl
4ai R = 4-trifluoromethylphenyl In another embodiment of the invention, the compound of formula 4 has structural formulae 4ba–4bi shown below:

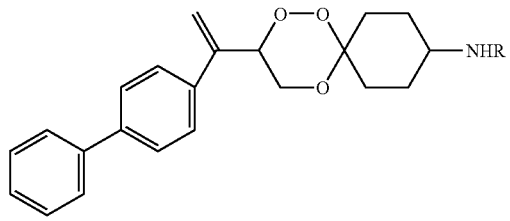

4ba R = 4-chlorophenyl
4bb R = 2-biphenyl (upper $R_f$)
4bc R = 2-biphenyl (lower $R_f$)
4bd R = 4-biphenyl
4be R = 2-fluorene
4bf R = 4-fluorophenyl
4bg R = 2-trifluoromethylphenyl
4bh R = 3-trifluoromethylphenyl
4bi R = 4-trifluoromethylphenyl In another embodiment of the invention, the compound of formula 4 has structural formulae 4ca–4cp shown below:

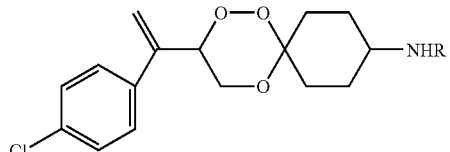

4ca R = phenyl
4cb R = 4-methoxyphenyl
4cc R = 4-chlorophenyl (upper $R_f$)
4cd R = 4-chlorophenyl (lower $R_f$)
4ce R = 3,5-dichlorophenyl (upper $R_f$)
4cf R = 3,5-dichlorophenyl (lower $R_f$)
4cg R = 4-acetylaminophenyl
4ch R = 1-naphthyl
4ci R = 2-biphenyl (upper $R_f$)
4cj R = 2-biphenyl (lower $R_f$)
4ck R = 4-biphenyl
4cl R = 2-fluorene
4cm R = 4-fluorophenyl
4cn R = 2-trifluoromethylphenyl
4co R = 3-trifluoromethylphenyl
4cp R = 4-trifluoromethylpenyl In another embodiment of the invention, the compound of formula 4 has structural formulae 4da–4dn shown below:

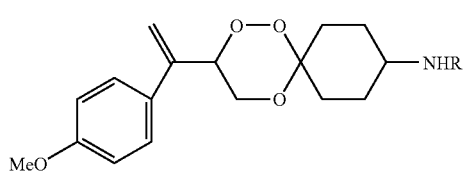

4da–4dn

4da R = phenyl
4db R = 4-methoxyphenyl
4dc R = 4-chlorophenyl
4dd R = 3,5-dichlorophenyl
4de R = 4-acetylaminophenyl
4df R = 1-naphthyl
4dg R = 2-biphenyl (upper R$_f$)
4dh R = 2-biphenyl (lower R$_f$)
4di R = 4-biphenyl
4dj R = 2-fluorene
4dk R = 4-fluorophenyl
4dl R = 2-trifluoromethylphenyl
4dm R = 3-trifluoromethylphenyl
4dn R = 4-trifluoromethylphenyl In another embodiment of the invention, the compound of formula 4 has structural formulae 4ea–4eo shown below:

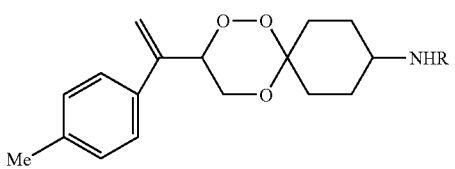

4ea–4eo

4ea R = phenyl
4eb R = 4-methoxyphenyl
4ec R = 4-chlorophenyl
4ed R = 3,5-dichlorophenyl (upper R$_f$)
4ee R = 3,5-dichlorophenyl (lower R$_f$)
4ef R = 4-acetylaminophenyl
4eg R = 1-naphthyl
4eh R = 2-biphenyl (upper R$_f$)
4ei R = 2-biphenyl (lower R$_f$)
4ej R = 4-biphenyl
4ek R = 2-fluorene
4el R = 4-fluorophenyl
4em R = 2-trifluoromethylphenyl
4en R = 3-trifluoromethylphenyl
4eo R = 4-trifluoromethylphenyl The present invention also provides a method for the preparation of a substituted amino functionalized-1,2,4-trioxanes of formula 4

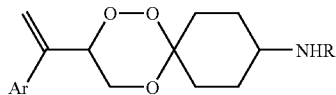

4 wherein Ar represents aryl groups selected from the groups consisting of phenyl, 4-biphenyl, 4-chlorophenyl, 4-methoxyphenyl and 4-methylphenyl and R represents phenyl, 4-methoxyphenyl, 4-chlorophenyl, 3,5-dichlorophenyl, 4-acetylaminophenyl, 1-naphthyl, 2-biphenyl, 4-biphenyl, 2-fluorene, 4-fluorophenyl, 2-trifluoromethylphenyl, 3-trifluoromethylphenyl and 4-trifluoromethylphenyl and the like, the process comprising reacting a keto trioxane of formula 3

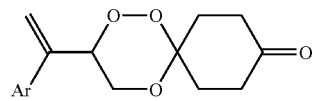

3 with an aromatic amine in the presence of NaBH(OAc)$_3$ in CH$_2$Cl$_2$ to furnish amino functionalized 1,2,4-trioxanes of formula 4.

In one embodiment of the invention, the aromatic amine is selected from the group consisting of aniline, 4-methoxyaniline, 4-chloroaniline, 3,5-dichloroaniline, 4-aminoacetanilide, 1-naphthylamine, 2-aminobiphenyl, 4-aminobiphenyl, 2-aminofluorene, 4-fluoroaniline, 2-trifluoromethylaniline, 3-trifluoromethylaniline and 4-trifluoromethylaniline.

In another embodiment of the invention, the compound of formula 4 is obtained by:

(i) Photooxygenating an allylic alcohol of formula 1 by passing oxygen gas or air in a solution of the alcohol in an organic solvent and in the presence of a dye and a light source which provides visible light, for a period of 4 h, to obtain a β-hydroxyhydroperoxide of formula 2

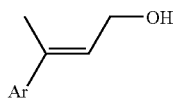

1

1a; Ar = Phenyl
1b; Ar = 4-Biphenyl
1c; Ar = 4-chlorophenyl
1d; Ar = 4-methoxyphenyl
1e; Ar = 4-methylphenyl

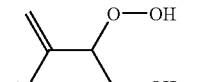

2

2a; Ar = Phenyl
2b; Ar = 4-Biphenyl
2c; Ar = 4-chlorophenyl
2d; Ar = 4-methoxyphenyl
2e; Ar = 4-methylphenyl (ii) reacting the hydroperoxides of formula 2 in situ with 1,4-cyclohexanedione in the presence of an acid catalyst to give a trioxane of formula 3;

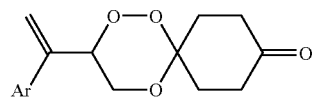

3

3a; Ar = Phenyl
3b; Ar = 4-Biphenyl
3c; Ar = 4-chlorophenyl
3d; Ar = 4-methoxyphenyl
3e; Ar = 4-methylphenyl (iii) reacting the keto trioxane of formula 3 with an aromatic amine in the presence of NaBH(OAc)$_3$ in CH$_2$Cl$_2$ to obtain amino functionalized 1,2,4-trioxane of formula 4.

In one embodiment of the invention, the aromatic amines is selected from the group consisting of aniline, 4-methoxyaniline, 4-chloroaniline, 3,5-dichloroaniline, 4-aminoacetanilide, 1-naphthylamine, 2-aminobiphenyl, 4-aminobiphenyl, 2-aminofluorene, 4-fluoroaniline, 2-trifluoromethylaniline, 3-trifluoromethylaniline and 4-trifluoromethylaniline.

The present invention also provides a method of treating a subject having malaria, comprising administering to the subject a pharmaceutically effective amount of a composition containing the substituted amino functionalized-1,2,4-trioxanes of formula 4, wherein Ar represents aryl groups selected from the groups consisting of phenyl, 4-biphenyl, 4-chlorophenyl, 4-methoxyphenyl and 4-methylphenyl and R represents phenyl, 4-methoxyphenyl, 4-chlorophenyl, 3,5-dichlorophenyl, 4-acetylaminophenyl, 1-naphthyl, 2-biphenyl, 4-biphenyl, 2-fluorene, 4-fluorophenyl, 2-trifluoromethylphenyl, 3-trifluoromethylphenyl and 4-trifluoromethylphenyl and a pharmaceutically acceptable carrier. The composition is administered intramuscularly or orally. The pharmaceutically acceptable amount of compound of formula 4 is in the range of 12 to 96 mg of compound of formula 4 per kilogram of body weight of subject per day.

DETAILED DESCRIPTION OF THE INVENTION

The present invention provides a process for the preparation of amino functionalized 1,2,4-trioxanes of formula 4 given above. Our SAR studies on amino functionalized 1,2,4-trioxanes have resulted in several novel amino functionalized 1,2,4-trioxanes with a high order of antimalarial activity against rodent malaria. The structures and activity of these compounds are disclosed here. The order of activity of amino functionalized 1,2,4-trioxanes reported here is much higher than amino functionalized 1,2,4-trioxanes reported by us earlier [Singh, C.; Malik, H.; Puri, S. K. *Bioorg. Med. Chem. Lett.* 2004, 14, 459]. The present invention also provides for the preparation of novel amino functionalized 1,2,4-trioxanes of formula 4 with high order of antimalarial activity. The present invention particularly relates to the preparation of amino functionalized 1,2,4-trioxanes of formula 4 wherein Ar represents phenyl, 4-biphenyl, 4-chlorophenyl, 4-methoxyphenyl, 4-methylphenyl and the like and R represents phenyl, 4-methoxyphenyl, 4-chlorophenyl, 3,5-dichlorophenyl, 4-acetylaminophenyl, 1-naphthyl, 2-biphenyl, 4-biphenyl, 2-fluorene, 4-fluorophenyl, 2-trifluoromethylphenyl, 3-trifluoromethylphenyl and 4-trifluoromethylphenyl and the like. These trioxanes are new compounds and are useful as antimalarial agents. These compounds have been tested against multidrug-resistant malaria in mice and have shown high order of antimalarial activity. The trioxanes thus hold promise of use for treatment of malaria, a highly prevalent parasitic disease. The amino functionalized 1,2,4-trioxanes of formula 4 are new chemical entities and have not been prepared earlier.

The process of the invention follows the general scheme shown below:

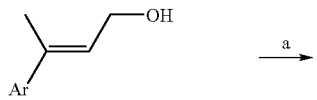

1a; Ar = Phenyl
1b; Ar = 4-Biphenyl
1c; Ar = 4-chlorophenyl
1d; Ar = 4-methoxyphenyl
1e; Ar = 4-methylphenyl

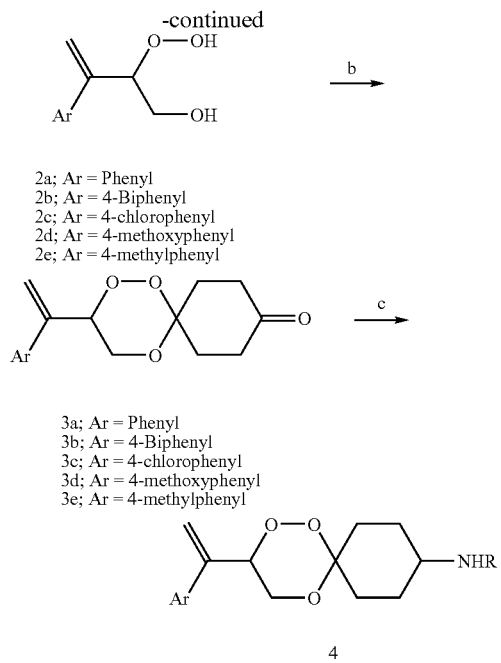

2a; Ar = Phenyl
2b; Ar = 4-Biphenyl
2c; Ar = 4-chlorophenyl
2d; Ar = 4-methoxyphenyl
2e; Ar = 4-methylphenyl 3a; Ar = Phenyl
3b; Ar = 4-Biphenyl
3c; Ar = 4-chlorophenyl
3d; Ar = 4-methoxyphenyl
3e; Ar = 4-methylphenyl

4

Scheme 1 Reagents and conditions: (a) hv, $O_2$, methylene blue, MeCN, −10 to 0° C., 4 h. (b) 1,4-cyclohexanedione, concd HCl, 5° C., 18 h. (c) $RNH_2$, $NaBH(OAc)_3$, $CH_2Cl_2$, π, 3.5 h.

Allylic alcohol of formula 1 was prepared by known procedure [(a) Singh, C. *Tetrahedron Lett.* 1990, 31, 6901. (b) Singh, C.; Tiwari, P.; Puri, S. K. PCT application No. PCT/1N02/00093 (28, Mar. 2002)]. Photooxygenation of allylic alcohols of formula 1 is effected by passing oxygen gas or air in the solution of alcohol in an organic solvent and in the presence of a dye and a light source which provides visible light, for a period of 4 h, to furnish β-hydroxyhydroperoxide of formula 2. The hydroperoxides of formula 2 are known compounds and have been prepared by us earlier [(a) Singh, C.; Misra, D.; Saxena, G.; Chandra, S. *Bioorg. Med. Chem. Lett.* 1992, 2, 497. (b) Singh, C.; Misra, D.; Saxena, G.; Chandra, S. *Bioorg. Med. Chem. Lett.* 1995, 5, 1913. (c) Singh, C.; Tiwari, P.; Puri, S. K. PCT Application No. PCT/1N02/00093 dated 28, Mar. 2002]. The dye acts as a sensitizer, i.e., converts $^3O_2$ to highly reactive $^1O_2$. Hydroperoxides of formula 2 are reacted in situ with 1,4-cyclohexanedione in the presence of an acid catalyst to give trioxanes of formula 3. These 1,2,4-trioxanes of formula 3 have been tested against malaria parasites in mice and show only moderate order of activity. Keto trioxanes 3a, 3b are known compounds as they have been prepared earlier by us [Singh, C.; Malik, H.; Puri, S. K. *Bioorg. Med. Chem. Lett.* 2004, 14, 459] while 3c, 3d, 3e are new compounds and have not been prepared earlier. Keto trioxanes of formula 3 are reacted with aromatic amines in the presence of $NaBH(OAc)_3$ in $CH_2Cl_2$ to furnish amino functionalized 1,2,4-trioxanes of formula 4. Aromatic amines used may be aniline, 4-methoxyaniline, 4-chloroaniline, 3,5-dichloroaniline, 4-aminoacetanilide, 1-naphthylamine, 2-aminobiphenyl, 4-aminobiphenyl, 2-aminofluorene, 4-fluoroaniline, 2-trifluoromethylaniline, 3-trifluoromethylaniline and 4-trifluoromethylaniline and the like. All the amino functionalized 1,2,4-trioxanes are new chemical entities and have not been prepared earlier. The amino functionalized 1,2,4-trioxanes of formula 4 have been tested against malaria parasites in mice and have shown high order of antimalarial activity.

This invention is further illustrated by the following examples which should not, however, be construed to limit the scope of the present invention.

Example 1

3-(1-Phenyl-Vinyl)-1,2,5-Trioxaspiro[5.5]undec-9-one (Compound 3a, Ar=phenyl)

Solution of allylic alcohol 1a (1 g, 6.75 mmol) and methylene blue (30 mg) in acetonitrile (100 ml) maintained at 0° C., was irradiated with 500 W tungsten-halogen lamp while oxygen was bubbled slowly into reaction mixture for 4 h. 1,4-Cyclohexanedione (1.15 g, 10.13 mmol) and concd. HCl (5 drops) were added and reaction mixture was left at 5° C. overnight.

Reaction mixture was concentrated under reduced pressure and residue taken up in ether (100 ml) was washed with sat. aq NaHCO$_3$ (30 ml). Aqueous layer was extracted with ether (2×75 ml), combined ether layer dried over anhyd. Na$_2$SO$_4$ and concentrated. Crude product was purified by column chromatography on silica gel using EtOAc-hexane (5:95) as eluant to furnish trioxane 3a (0.94 g, 51% yield, based on allylic alcohol 1a used), m.p. 70–71° C.

Example 2

(4-Chloro-Phenyl)-[3-(1-Phenyl-Vinyl)-1,2,5-Trioxa-Spiro[5.5]undec-9-yl]-Amine (Compound 4aa, Formula 4, Ar=Phenyl, R=4-Chlorophenyl)

Acetic acid (1 ml) is added to mixture of trioxane 3a (0.4 g, 1.45 mmol) and 4-chloroaniline (0.23 g, 1.82 mmol) in dichloromethane (20 ml). Reaction mixture was stirred at room temp for half an hour. Sodium triacetoxyborohydride (0.46 g, 3.63 mmol) was added slowly and was stirred for 3 h at room temperature. Reaction mixture was then poured into water and extracted with CH$_2$Cl$_2$ (2×20 ml). Combined organic layer was dried over anhyd. Na$_2$SO$_4$, concentrated under vacuum. Crude product was chromatographed over silica gel using benzene-hexane (50:50) as eluant to furnish amino functionalized 1,2,4-trioxane 4aa as an inseparable mixture of diastereomers as oil (0.40 g, 71.7% yield).

Example 3

Biphenyl-2-yl-[3-(1-Phenyl-Vinyl)-1,2,5-Trioxa-Spiro[5.5]undec-9-yl]Amine (Compound 4ab and 4ac, Formula 4, Ar=Phenyl, R=2-Biphenyl)

To mixture of trioxane 3a (0.50 g, 1.82 mmol) and 2-aminobiphenyl (0.38 g, 2.27 mmol) in dichloromethane (20 ml) acetic acid was added (1 ml) and reaction mixture was stirred at room temp for half an hour. Sodium triacetoxyborohydride (0.58 g, 2.73 mmol) was added slowly and it was stirred for 3 h at room temperature. The reaction mixture was then poured into water and extracted with CH$_2$Cl$_2$ (2×20 ml). Combined organic layer was dried over anhyd. Na$_2$SO$_4$, concentrated under vacuum and crude product was chromatographed over silica gel using benzene-hexane (50:50) as eluant to furnish amino functionalized 1,2,4-trioxane 4ab as oil (upper $R_f$, 0.17 g, 21.8% yield) and 4ac (lower $R_f$, 0.25 g, 32.6% yield), m.p. 74–76° C.

Example 4

Biphenyl-4-yl-[3-(1-Phenyl-Vinyl)-1,2,5-Trioxa-Spiro[5.5]undec-9-yl]Amine (Compound 4ad, Formula 4, Ar=Phenyl, R=4-Biphenyl)

To a mixture of trioxane 3a (0.40 g, 1.45 mmol) and 4-aminobiphenyl (0.30 g, 1.82 mmol) in dichloromethane (20 ml) acetic acid (1 ml) was added and reaction mixture was stirred at room temp for half an hour. Sodium triacetoxyborohydride (0.46 g, 3.63 mmol) was added slowly and it was stirred for 3 h at room temperature. Reaction mixture was then poured into water and extracted with CH$_2$Cl$_2$ (2×20 ml). Combined organic layer was dried over anhyd. Na$_2$SO$_4$, concentrated under vacuum and crude product was chromatographed over silica gel using benzene-hexane (50:50) as eluant to furnish amino functionalized 1,2,4-trioxane 4ad as an inseparable mixture of diastereomers (0.44 g, 70.5% yield), m.p. 118–120° C.

Example 5

(9H-Fluoren-3-yl)-[1-Phenyl-Vinyl)-1,2,5-Trioxa-Spiro[5.5]undec-9-yl]-Amine (Compound 4ae, Formula 4, Ar=Phenyl, R=2-Fluorene)

To a mixture of trioxane 3a (0.30 g, 1.09 mmol) and 2-aminofluorene (0.24 g, 1.36 mmol) in dichloromethane (20 ml) was added acetic acid (1 ml) and reaction mixture was stirred at room temp for half an hour. Sodium triacetoxyborohydride (0.35 g, 1.64 mmol) was added slowly and it was stirred for 3 h at room temperature. The reaction mixture was then poured into water and extracted with CH$_2$Cl$_2$ (2×15 ml). Combined organic layer was dried over anhyd. Na$_2$SO$_4$, concentrated under vacuum and the crude product was chromatographed over silica gel using benzene-hexane (50:50) as eluant to furnish amino functionalized 1,2,4-trioxane 4ae as an inseparable mixture of diastereomers (0.30 g, 63.5% yield), m.p. 144–146° C.

Example 6

(4-Fluoro-Phenyl)-[3-(1-Phenyl-Vinyl)-1,2,5-Trioxa-Spiro[5.5]undec-9-yl]-Amine (Compound 4af, Formula 4, Ar=Phenyl, R=4-Fluorophenyl)

To a mixture of trioxane 3a (0.30 g, 1.09 mmol) and 4-fluoroaniline (0.15 g, 1.34 mmol) in dichloromethane (20 ml) was added acetic acid (1 ml) and reaction mixture was stirred at room temp for half an hour. Sodium triacetoxyborohydride (0.35 g, 1.65 mmol) was added slowly and it was stirred for 3 h at room temperature. The reaction mixture was then poured into water and extracted with CH$_2$Cl$_2$ (2×20 ml). Combined organic layer was dried over anhyd. Na$_2$SO$_4$, concentrated under vacuum and the crude product was chromatographed over silica gel using benzene-hexane (50:50) as eluant to furnish amino functionalized 1,2,4-trioxane 4af as an inseparable mixture of diastereomers as oil (0.34 g, 84.1% yield).

Example 7

[3-(1-Phenyl-Vinyl)-1,2,5-Trioxa-Spiro[5.5]undec-9-yl]-(3-Trifluoromethyl-Phenyl)-Amine (Compound 4ah, Formula 4, Ar=Phenyl, R=3-Trifluoromethylphenyl)

To a mixture of trioxane 3a (0.50 g, 1.82 mmol) and 3-trifluoromethylaniline (0.37 g, 2.27 mmol) in dichloromethane (20 ml) was added acetic acid (1 ml) and reaction mixture was stirred at room temp for half an hour. Sodium triacetoxyborohydride (0.60 g, 2.73 mmol) was added slowly and it was stirred for 3 h at room temperature. The reaction mixture was then poured into water and extracted with $CH_2Cl_2$ (2×20 ml). Combined organic layer was dried over anhyd. $Na_2SO_4$, concentrated under vacuum and the crude product was chromatographed over silica gel using benzene-hexane (50:50) as eluant to furnish amino functionalized 1,2,4-trioxane 4ah as an inseparable mixture of diastereomers as oil (0.49 g, 64.1% yield).

Example 8

[3-(1-Phenyl-Vinyl)-1,2,5-Trioxa-Spiro[5.5]undec-9-yl]-(4-Trifluoromethyl-Phenyl-Amine (Compound 4ai, Formula 4, Ar=Phenyl, R=4-Trifluoromethylphenyl)

To a mixture of trioxane 3a (0.30 g, 1.09 mmol) and 4-trifluoromethylaniline (0.22, 1.36 mmol) dichloromethane (20 ml) was added acetic acid (1 ml) and reaction mixture was stirred at room temp for half an hour. Sodium triacetoxyborohydride (0.34 g, 1.60 mmol) was added slowly and it was stirred for 3 h at room temperature. The reaction mixture was then poured into water and extracted with $CH_2Cl_2$ (2×20 ml). Combined organic layer was dried over anhyd. $Na_2SO_4$, concentrated under vacuum and the crude product was chromatographed over silica gel using benzene-hexane (50:50) as eluant to furnish amino functionalized 1,2,4-trioxane 4ai as an inseparable mixture of diastereomers as oil (0.26 g, 58.7% yield).

Example 9

3-(1-Biphenyl-4yl-Vinyl)-1,2,5-Trioxaspiro[5.5]undec-9-one (Compound 3b, Ar=Biphenyl)

Solution of allylic alcohol 1 h (1 g, 6.75 mmol) and methylene blue (30 mg) in acetonitrile (100 ml) maintained at 0° C., was irradiated with 500 W tungsten-halogen lamp while oxygen was bubbled slowly into reaction mixture for 4 h. 1,4-Cyclohexanedione (1.15 g, 10.13 mmol) and concd HCl (5 drops) were added and the reaction mixture was left at 5° C. overnight. Reaction mixture was concentrated under reduced pressure and residue taken up in either (100 ml) was washed with sat. aq $NaHCO_3$ (30 ml). The aqueous layer was extracted with ether (2×75 ml), combined ether layer dried over anhyd. $Na_2SO_4$ and concentrated. The crude product was purified by column chromatography on silica gel using EtOAc-hexane (5:95) as eluant to furnish trioxane 3b (0.65 g, 42% yield, based on allylic alcohol 1b used), m.p. 104–105° C.

Example 10

[3-(1-Biphenyl-4-yl-Vinyl)-1,2,5-Trioxa-Spiro[5.5]undec-9-yl]-(4-Chloro-Phenyl)-Amine (Compound 4ba, Formula 4, Ar=4-Biphenyl, R=4-Chlorophenyl)

To a mixture of trioxane 3b (0.40 g, 1.14 mmol) and 4-chloroaniline (0.18 g, 1.42 mmol) in dichloromethane (20 ml) was added acetic acid (1 ml) and reaction mixture was stirred at room temp for half an hour. Sodium triacetoxyborohydride (0.36 g, 1.71 mmol) was added slowly and it was stirred for 3 h at room temperature. The reaction mixture was then poured into water and extracted with $CH_2Cl_2$ (2×15 ml). Combined organic layer was dried over anhyd. $Na_2SO_4$, concentrated under vacuum and the crude product was chromatographed over silica gel using benzene-hexane (50:50) as eluant to furnish amino functionalized 1,2,4-trioxane 4ba as an inseparable mixture of diastereomers (0.38 g, 72.1% yield), m.p. 148–150° C.

Example 11

Biphenyl-2-yl-[3-(1-Biphenyl-4-yl-Vinyl)-1,2,5-Trioxaspiro[5.5]undec-9-yl]-Amine (Compound 4bb and 4bc, Formula 4, Ar=4-Biphenyl, R=2-Biphenyl)

Acetic acid (1 ml) is added to mixture of trioxane 3b (0.60 g, 1.71 mmol) and 2-aminobiphenyl (0.36 g, 2.14 mmol) in dichloromethane (25 ml). Reaction mixture was stirred at room temp for half an hour. Sodium triacetoxyborohydride (0.54 g, 2.57 mmol) was added slowly and it was stirred for 3 h at room temperature. Reaction mixture was then poured into water and extracted with $CH_2Cl_2$ (2×25 ml). Combined organic layer was dried over anhyd. $Na_2SO_4$, concentrated under vacuum. Crude product was chromatographed over silica gel using eluant benzene-hexane (50:50) to give amino functionalized 1,2,4-trioxane 4bb (upper $R_f$, 0.19 g, 21.7% yield), m.p. 105–106° C. and 4bc (lower $R_f$, 0.28 g, 32.4% yield), mp 148–150° C.

Example 12

Biphenyl-4-yl-[3-(1-Biphenyl-4-yl-Vinyl)-1,2,5-trioxaspiro[5.5]undec-9-yl]-Amide (Compound 4bd, Formula 4, Ar=4-Biphenyl, R=4-Biphenyl)

To mixture of trioxane 3b (0.50 g, 1.42 mmol) and 4-aminobiphenyl (0.30 g, 1.78 mmol) in dichloromethane (20 ml) was added acetic acid (1 ml) and reaction mixture was stirred at room temp for half an hour. Sodium triacetoxyborohydride (0.45 g, 2.14 mmol) was added slowly and it was stirred for 3 h at room temperature. The reaction mixture was then poured into water and extracted with $CH_2Cl_2$ (2×20 ml). Combined organic layer was dried over anhyd. $Na_2SO_4$, concentrated under vacuum and the crude product was chromatographed over silica gel using benzene-hexane (50:50) as eluant to furnish amino functionalized 1,2,4-trioxane 4bd as an inseparable mixture of diastereomers (0.53 g, 73.8% yield), m.p. 158–160° C.

Example 13

[3-(1-Biphenyl-4-yl-Vinyl)-1,2,5-Trioxa-Spiro[5.5]undec-9-yl]-(9H-Fluoren-3-yl)-Amine (Compound 4be, Formula 4, Ar=4-Biphenyl, R=2-Fluorene)

To a mixture of trioxane 3b (0.30 g, 0.85 mmol) and 2-aminofluorene (0.19 g, 1.07 mmol) in dichloromethane (20 ml) was added acetic acid (1 ml) and reaction mixture was stirred at room temp for half an hour. Sodium triacetoxyborohydride (0.27 g, 1.64 mmol) was added slowly and it was stirred for 3 h at room temperature. The reaction mixture was then poured into water and extracted with $CH_2Cl_2$ (2×15 ml). Combined organic layer was dried over anhyd. $Na_2SO_4$, concentrated under vacuum and the crude product was chromatographed over silica gel using benzene-hexane (50:50) as eluant to furnish amino functionalized 1,2,4-trioxane 4be as an inseparable mixture of diastereomers (0.28 g, 65.04% yield), m.p. 170–172° C.

Example 14

3-[1-(4-Chloro-Phenyl)-Vinyl]-1,2,5-Trioxa-Spiro [5.5]undecan-9-one (Compound 3c, Ar=4-Chlorophenyl)

Solution of allylic alcohol 1c (1 g, 5.47 mmol) and methylene blue (30 mg) in acetonitrile (100 ml) maintained at 0° C., was irradiated with 500 W tungsten-halogen lamp while oxygen was bubbled slowly into reaction mixture for 4 h. 1,4-Cyclohexanedione (1.22 g, 10.95 mmol) and concd HCl (5 drops) were added and the reaction mixture was left at 5° C. overnight. Reaction mixture was concentrated under reduced pressure and residue taken up in ether (100 ml) was washed with sat. aq $NaHCO_3$ (30 ml). The aqueous layer was extracted with ether (2×75 ml), combined ether layer dried over anhyd. $Na_2SO_4$ and concentrated. The crude product was purified by column chromatography on silica gel using EtOAc-hexane (5:95) as eluant to furnish trioxane 3c (0.64 g, 38% yield, based on allylic alcohol 1c used), m.p. 72–74° C.

Example 15

{3-[1-(4-Chloro-Phenyl)-Vinyl]-1,2,5-Trioxa-Spiro [5.5]undec-9-yl}-Phenyl-Amine (Compound 4ca, Formula 4, Ar=4-Chlorophenyl, R=Phenyl)

To mixture of trioxane 3c (0.50 g, 1.62 mmol) and aniline (0.19 g, 2.02 mmol) in dichloromethane (20 ml) was added acetic acid (1 ml) and reaction mixture was stirred at room temp for half an hour. Sodium triacetoxyborohydride (0.51 g, 2.43 mmol) was added slowly and it was stirred for 3 h at room temperature. The reaction mixture was then poured into water and extracted with $CH_2Cl_2$ (2×20 ml). Combined organic layer was dried over anhyd. $Na_2SO_4$, concentrated under vacuum and the crude product was chromatographed over silica gel using benzene-hexane (50:50) as eluant to furnish amino functionalized 1,2,4-trioxane 4ca as an inseparable mixture of diastereomers as oil (0.45 g, 73.4% yield)

Example 16

{3-[1-(4-Chloro-Phenyl)-Vinyl]-1,2,5-Trioxa-Spiro [5.5]undec-9-yl}-p-Tolyl-Amine (Compound 4cd, Formula 4, Ar=4-Chlorophenyl, R=4-Methoxyphenyl)

To mixture of trioxane 3c (0.50 g, 2.27 mmol) and 4-methoxyaniline (0.25 g, 2.02 mmol) in dichloromethane (20 ml) was added acetic acid (1 ml) and reaction mixture was stirred at room temp for half an hour. Sodium triacetoxyborohydride (0.51 g, 2.43 mmol) was added slowly and it was stirred for 3 h at room temperature. The reaction mixture was then poured into water and extracted with $CH_2Cl_2$ (2×20 ml). Combined organic layer was dried over anhyd. $Na_2SO_4$, concentrated under vacuum and the crude product was chromatographed over silica gel using benzene-hexane (50:50) as eluant to furnish amino functionalized 1,2,4-trioxane as an inseparable mixture of diastereomers 4cd (0.54 g, 80.2% yield), m.p. 148–150° C.

Example 17

Biphenyl-2-yl-{3-[1-(4-Chloro-Phenyl)-Vinyl]-1,2, 5-Trioxa-Spiro[5.5]undec-9-yl}-Amine (Compound 4ci and 4cj, Formula 4, Ar=4-Chlorophenyl, R=2-Biphenyl)

To a mixture of trioxane 3c (0.50 g, 1.62 mmol) and 2-aminobiphenyl (0.34 g, 2.02 mmol) in dichloromethane (20 ml) was added acetic acid (1 ml) and reaction mixture was stirred at room temp for half an hour. Sodium triacetoxyborohydride (0.51 g, 2.43 mmol) was added slowly and it was stirred for 3 h at room temperature. The reaction mixture was then poured into water and extracted with $CH_2Cl_2$ (2×20 ml). Combined organic layer was dried over anhyd. $Na_2SO_4$, concentrated under vacuum and the crude product was chromatographed over silica gel using benzene-hexane (50:50) as eluant to furnish amino functionalized 1,2,4-trioxane 4ci (upper $R_f$, 0.21 g, 28.8% yield) and 4cj (lower $R_f$, 0.32 g, 43.2% yield) as oil.

Example 18

Biphenyl-4-yl-{3-[1-(4-Chloro-Phenyl)-Vinyl]-1,2, 5-Trioxa-Spiro[5.5]undec-9-yl}-Amine (Compound 4ck, Formula 4, Ar=4-Chlorophenyl, R=4-Biphenyl)

To a mixture of trioxane 3c (0.50 g, 1.62 mmol) and 4-aminobiphenyl (0.34 g, 2.02 mmol) in dichloromethane (20 ml) was added acetic acid (1 ml) and reaction mixture was stirred at room temp for half an hour. Sodium triacetoxyborohydride (0.51 g, 2.43 mmol) was added slowly and it was stirred for 3 h at room temperature. The reaction mixture was then poured into water and extracted with $CH_2Cl_2$ (2×20 ml). Combined organic layer was dried over anhyd. $Na_2SO_4$, concentrated under vacuum and the crude product was chromatographed over silica gel using benzene-hexane (50:50) as eluant to furnish amino functionalized 1,2,4-trioxane 4ck as an inseparable mixture of diastereomers as oil (0.37 g, 49.4% yield).

Example 19

{3-[1-(4-Chloro-Phenyl)-Vinyl]-1,2,5-Trioxa-Spiro [5.5]undec-9-yl}-(9H-Fluoren-3yl)-Amine (Compound 4cl, Formula 4, Ar=4-Chlorophenyl, R=2-Fluorene)

To a mixture of trioxane 3c (0.30 g, 0.97 mmol) and 2-aminofluorene (0.22 g, 1.21 mmol) in dichloromethane (20 ml) was added acetic acid (1 ml) and reaction mixture was stirred at room temp for half an hour. Sodium triacetoxyborohydride (0.30 g, 1.46 mmol) was added slowly and it was stirred for 3 h at room temperature. The reaction mixture was then poured into water and extracted with $CH_2Cl_2$ (2×15 ml). Combined organic layer was dried over anhyd. $Na_2SO_4$, concentrated under vacuum and the crude product was chromatographed over silica gel using benzene-hexane (50:50) as eluant to furnish amino functionalized 1,2,4-trioxane 4cl as an inseparable mixture of diastereomers (0.19 g, 42.3% yield), m.p. 162–164° C.

Example 20

{3-[1-(4-Chloro-Phenyl)-Vinyl]-1,2,5-Trioxa-Spiro [5.5]undec-9-yl}-(4-Trifluoromethyl-Phenyl)-Amine (Compound 4cp, Formula 4, Ar=4-Chlorophenyl, R=4-Trifluoromethylphenyl)

To mixture of trioxane 3c (0.30 g, 0.97 mmol) and 4-trifluoromethylaniline (0.19 g, 1.21 mmol) in dichloromethane (20 ml) was added acetic acid (1 ml) and reaction mixture was stirred at room temp for half an hour. Sodium triacetoxyborohydride (0.30 g, 1.46 mmol) was added slowly and it was stirred for 3 h at room temperature. Reaction mixture was then poured into water and extracted with $CH_2Cl_2$ (2×15 ml). Combined organic layer was dried over anhyd. $Na_2SO_4$, concentrated under vacuum and crude product was chromatographed over silica gel using benzene-hexane (50:50) as eluant to furnish amino functionalized 1,2,4-trioxane 4cp as an inseparable mixture of diastereomers as oil (0.21 g, 47.6% yield).

Example 21

3-[1-(4-Methoxy-Phenyl)-Vinyl]-1,2,5-Trioxa-Spiro [5.5]undecan-9-one (Compound 3d, Ar=4-Methoxyphenyl)

Solution of allylic alcohol 1d (1 g, 5.61 mmol) and methylene blue (30 mg) in acetonitrile (100 ml) maintained at 0° C., was irradiated with a 500 W tungsten-halogen lamp while oxygen was bubbled slowly into the reaction mixture for 4 h. 1,4-Cyclohexanedione (1.25 g, 11.22 mmol) and concd HCl (5 drops) were added and the reaction mixture was left at 5° C. overnight. Reaction mixture was concentrated under reduced pressure and residue taken up in ether (100 ml) was washed with sat. aq $NaHCO_3$ (30 ml). Aqueous layer was extracted with ether (2×75 ml), combined ether layer dried over anhyd. $Na_2SO_4$ and concentrated. Crude product was purified by column chromatography on silica gel using EtOAc-hexane (5:95) as eluant to furnish trioxane 3d as oil (0.48 g, 28.1% yield, based on allylic alcohol 1d used).

Example 22

{3-[1-(4-Methoxy-Phenyl)-Vinyl]-1,2,5-Trioxa-Spiro[5.5]undec-9-yl}-Phenyl-Amine (Compound 4da, Formula 4, Ar=4-Methoxyphenyl, R=Phenyl)

To a mixture of trioxane 3d (0.50 g, 1.62 mmol) and aniline (0.19 g, 2.05 mmol) in dichloromethane (20 ml) was added acetic acid (1 ml) and reaction mixture was stirred at room temp for half an hour. Sodium triacetoxyborohydride (0.52 g, 2.46 mmol) was added slowly and it was stirred for 3 h at room temperature. The reaction mixture was then poured into water and extracted with $CH_2Cl_2$ (2×20 ml). Combined organic layer was dried over anhyd. $Na_2SO_4$, concentrated under vacuum and the crude product was chromatographed over silica gel using benzene-hexane (50:50) as eluant to furnish amino functionalized 1,2,4-trioxane 4da as an inseparable mixture of diastereomers as oil (0.47 g, 74.9% yield).

Example 23

(4-Methoxy-Phenyl)-{3-[1-(4-Methoxy-Phenyl)-Vinyl]-1,2,5-Trioxa-Spiro [5.5]undec-9-yl}-Amine (Compound 4db, Formula 4, Ar=4-Methoxyphenyl, R=4-Methoxyphenyl)

To a mixture of trioxane 3d (0.50 g, 1.54 mmol) and 4-methoxyaniline (0.25 g, 2.05 mmol) in dichloromethane (20 ml) was added acetic acid (1 ml) and reaction mixture was stirred at room temp for half an hour. Sodium triacetoxyborohydride (0.52 g, 2.46 mmol) added slowly and it was stirred for 3 h at room temperature. The reaction mixture was then poured into water and extracted with $CH_2Cl_2$ (2×20 ml). Combined organic layer was dried over anhyd. $Na_2SO_4$, concentrated under vacuum and the crude product was chromatographed over silica gel using benzene-hexane (50:50) as eluant to furnish amino functionalized 1,2,4-trioxane 4db as an inseparable mixture of diastereomers (0.53 g, 79.2% yield), m.p. 126–128° C.

Example 24

(4-Chloro-Phenyl)-{3-[1-(4-Methoxy-Phenyl)-Vinyl]-1,2,5-Trioxa-Spiro[5.5]undec-9-yl}-Amine (Compound 4dc, Formula 4, Ar=4-Methoxyphenyl, R=4-Chlorophenyl)

To a mixture of trioxane 3d (0.50 g, 1.62 mmol) and 4-chloroaniline (0.19 g, 2.05 mmol) in dichloromethane (20 ml) was added acetic acid (1 ml) and reaction mixture was stirred at room temp for half an hour. Sodium triacetoxyborohydride (0.52 g, 2.46 mmol) was added slowly and it was stirred for 3 h at room temperature. The reaction mixture was then poured into water and extracted with $CH_2Cl_2$ (2×20 ml). Combined organic layer was dried over anhyd. $Na_2SO_4$, concentrated under vacuum and the crude product was chromatographed over silica gel using benzene-hexane (50:50) as eluant to furnish amino functionalized 1,2,4-trioxane 4dc as an inseparable mixture of diastereomers (0.47 g, 74.9% yield), m.p. 104–106° C.

Example 25

(3,5-Dichloro-Phenyl)-{3-[1-(4-Methoxy-Phenyl)-Vinyl]-1,2,5-Trioxa-Spiro[5.5]undec-9-yl}-Amine (Compound 4dd, Formula 4, Ar=4-Methoxyphenyl, R=3,5-Dichlorophenyl)

To mixture of trioxane 3d (0.50 g, 1.64 mmol) and 3,5-dichloroaniline (0.33 g, 2.05 mmol) in dichloromethane (20 ml) was added acetic acid (1 ml) and reaction mixture was stirred at room temp for half an hour. Sodium triacetoxyborohydride (0.52 g, 2.46 mmol) was added slowly and it was stirred for 3 h at room temperature. The reaction mixture was then poured into water and extracted with $CH_2Cl_2$ (2×20 ml). Combined organic layer was dried over anhyd. $Na_2SO_4$, concentrated under vacuum and the crude product was chromatographed over silica gel using benzene-hexane (50:50) as eluant to furnish amino functionalized 1,2,4-trioxane 4dd as an inseparable mixture of diastereomers (0.38 g, 51.3% yield), m.p. 85–86° C.

Example 26

N-(4-{3-[1-(4-Methoxy-Phenyl)-Vinyl]-1,2,5-Tri-oxa-Spiro[5.5]undec-9-ylamino}-Phenyl)-Acetamide (Compound 4de, Formula 4, Ar=4-Methoxyphenyl, R=4-Acetylaminophenyl)

To a mixture of trioxane 3d (0.50 g, 1.64 mmol) and 4-aminoacetanilide (0.30 g, 2.05 mmol) in dichloromethane (20 ml) was added acetic acid (1 ml) and reaction mixture was stirred at room temp for half an hour. Sodium triacetoxyborohydride (0.52 g, 2.46 mmol) was added slowly and it was stirred for 3 h at room temperature. The reaction mixture was then poured into water and extracted with $CH_2Cl_2$ (2×20 ml). Combined organic layer was dried over anhyd. $Na_2SO_4$, concentrated under vacuum and the crude product was chromatographed over silica gel using EtOAc-hexane (50:50) as eluant to furnish amino functionalized 1,2,4-trioxane 4de as an inseparable mixture of diastereomers (0.60 g, 83.3% yield), m.p. 70–72° C.

Example 27

{3-[1-(4-Methoxy-Phenyl)-Vinyl]-1,2,5-Trioxa-Spiro[5.5]undec-9-yl}-(3-Trifluoromethyl-Phenyl)-Amine (Compound 4dm, Formula 4, Ar=4-Methoxyphenyl, R=3-Trifluoromethylphenyl)

To mixture of trioxane 3d (0.30 g, 0.98 mmol) and 3-trifluoromethylaniline (0.20 g, 1.21 mmol) in dichloromethane (20 ml) was added acetic acid (1 ml) and reaction mixture was stirred at room temp for half an hour. Sodium triacetoxyborohydride (0.31 g, 1.47 mmol) was added slowly and it was stirred for 3 h at room temperature. Reaction mixture was then poured into water and extracted with $CH_2Cl_2$ (2×15 ml). Combined organic layer was dried over anhyd. $Na_2SO_4$, concentrated under vacuum and crude product was chromatographed over silica gel using EtOAc-hexane (50:50) as eluant to furnish amino functionalized 1,2,4-trioxane 4dm as an inseparable mixture of diastereomers as oil (0.27 g, 60.9% yield).

Example 28

3-(1-p-Tolyl-Vinyl)-1,2,5-Trioxa-Spiro[5.5]undecan-9-one (Compound 3e, Ar=4-Methylphenyl)

Solution of allylic alcohol 1e (1 g, 6.16 mmol) and methylene blue (30 mg) in acetonitrile (100 ml) maintained at 0° C. was irradiated with a 500 W tungsten-halogen lamp while oxygen was bubbled slowly into reaction mixture for 4 h. 1,4-Cyclohexanedione (1.15 g, 10.13 mmol) and concd HCl (5 drops) were added and reaction mixture was left at 5° C. overnight. Reaction mixture was concentrated under reduced pressure and residue taken up in ether (100 ml) was washed with sat. aq $NaHCO_3$ (30 ml). The aqueous layer was extracted with ether (2×75 ml), combined ether layer dried over anhyd. $Na_2SO_4$ and concentrated. The crude product was purified by column chromatography on silica gel using EtOAc-hexane (5:95) as eluant to furnish trioxane 3e (0.58 g, 32.7% yield, based on allylic alcohol 1e used), m.p. 66–68° C.

Example 29

Phenyl-[3-(1-p-Tolyl-Vinyl)-1,2,5-Trioxa-Spiro[5.5]undec-9-yl]-Amine (Compound 4ea, Formula 4, Ar=4-Methylphenyl, R=Phenyl)

To a mixture of trioxane 3e (0.30 g, 1.04 mmol) and aniline (0.12 g, 1.30 mmol) in dichloromethane (20 ml) was added acetic acid (1 ml) and reaction mixture was stirred at room temp for half an hour. Sodium triacetoxyborohydride (0.33 g, 1.56 mmol) was added slowly and it was stirred for 3 h at room temperature. The reaction mixture was then poured into water and extracted with $CH_2Cl_2$ (2×20 ml). Combined organic layer was dried over anhyd. $Na_2SO_4$, concentrated under vacuum and the crude product was chromatographed over silica gel using benzene-hexane (50:50) as eluant to furnish amino functionalized 1,2,4-trioxane 4ea as an inseparable mixture of diastereomers as oil (0.29 g, 76.3% yield).

Example 30

(4-Methoxy-Phenyl)-[3-(1-p-Tolyl-Vinyl)-1,2,5-Trioxa-Spiro[5.5]undec-9-yl]-Amine (Compound 4eb, Formula 4, Ar=4-Methylphenyl, R=4-Methoxyphenyl)

To a mixture of trioxane 3e (0.30 g, 1.04 mmol) and 4-methoxyaniline (0.16 g, 1.30 mmol) in dichloromethane (20 ml) was added acetic acid (1 ml) and reaction mixture was stirred at room temp for half an hour. Sodium triacetoxyborohydride (0.33 g, 1.56 mmol) was added slowly and it was stirred for 3 h at room temperature. The reaction mixture was then poured into water and extracted with $CH_2Cl_2$ (2×15 ml). Combined organic layer was dried over anhyd. $Na_2SO_4$, concentrated under vacuum and the crude product was chromatographed over silica gel using benzene-hexane (50:50) as eluant to furnish amino functionalized 1,2,4-trioxane 4eb as an inseparable mixture of diastereomers as oil (0.33 g, 80.2% yield).

Example 31

(4-Chloro-Phenyl)-[3-(1-p-Tolyl-Vinyl)-1,2,5-Trioxa-Spiro[5.5]undec-9-yl]-Amine (Compound 4ec Formula 4, Ar=4-Methylphenyl, R=4-Chlorophenyl)

Acetic acid (1 ml) is added to mixture of trioxane 3e (0.30 g, 1.04 mmol) and 4-chloroaniline (0.16 g, 1.30 mmol) in dichloromethane (20 ml). Reaction mixture was stirred at room temp for half an hour. Sodium triacetoxyborohydride (0.33 g, 1.56 mmol) was added slowly and it was stirred for 3 h at room temperature. Reaction mixture was then poured into water and extracted with $CH_2Cl_2$ (2×15 ml). Combined organic layer was dried over anhyd. $Na_2SO_4$, concentrated under vacuum. Crude product was chromatographed over silica gel using benzene-hexane (50:50) as eluant to furnish amino functionalized 1,2,4-trioxane 4ec as an inseparable mixture of diastereomers (0.26 g, 62.6% yield), m.p. 110–112° C.

Example 32

(3,5-Dichloro-Phenyl)-[3-(1-Tolyl-Vinyl)-1,2,5-Trioxa-Spiro[5.5]undec-9-yl]-Amine (Compound 4ed (upper Rf) and 4ee (lower Rf), Formula 4, Ar=4-Methylphenyl, R=3,5-Dichlorophenyl)

Acetic acid (1 ml) is added to mixture of trioxane 3e (0.50 g, 1.62 mmol) and 3,5-dichloroanile (0.19 g, 2.05 mmol) in dichloromethane (20 ml) and reaction mixture stirred at room temp for half an hour. Sodium triacetoxyborohydride (0.52 g, 2.46 mmol) was added slowly and stirred for 3 h at room temperature. Reaction mixture was poured into water and extracted with $CH_2Cl_2$ (2×20 ml). Combined organic layer was dried over anhyd. $Na_2SO_4$, concentrated under vacuum. Crude product chromatographed over silica gel using benzene-hexane (50:50) as eluant to furnish amino functionalized 1,2,4-trioxane 4ed (upper $R_f$, 0.19 g, 25.20% yield), m.p. 140–142° C. and 4ee (lower $R_f$, 0.28 g, 37.1% yield), m.p. 112–114° C.

Example 33

N-{4-[3-(1-p-Tolyl-Vinyl)-1,2,5-Trioxa-Spiro[5.5] undec-9-ylamino]-Phenyl}-Acetamide (Compound 4ef, Formula 4, Ar=4-Methylphenyl, R=4-Acetylaminophenyl)

Acetic acid (1 ml) was added to mixture of trioxane 3e (0.50 g, 1.62 mmol) and 4-aminoacetanilide (0.19 g, 2.05 mmol) in dichloromethane (20 ml). Reaction mixture was stirred at room temp for half an hour. Sodium triacetoxyborohydride (0.52 g, 2.46 mmol) was added slowly and stirred for 3 h at room temperature. Reaction mixture was then poured into water and extracted with $CH_2Cl_2$ (2×20 ml). Combined organic layer was dried over anhyd. $Na_2SO_4$, and concentrated under vacuum. Crude product was chromatographed over silica gel using EtOAc-hexane (50:50) as eluant to furnish amino functionalized 1,2,4-trioxane 4ef as an inseparable mixture of diastereomers (0.47 g, 76.2% yield), m.p. 83–85° C.

Example 34

Naphthalen-1-yl-[3-(1-p-Tolyl-Vinyl)-1,2,5-Trioxa-Spiro[5.5]undec-9-yl]-Amine (Compound 4eg, Formula 4, Ar=4-Methylphenyl, R=1-Naphthyl)

Acetic acid (1 ml) was added to mixture of trioxane 3e (0.50 g, 1.64 mmol) and 1-naphthylamine (0.30 g, 2.05 mmol) in dichloromethane (20 ml). Reaction mixture was stirred at room temperature for half an hour. Sodium triacetoxyborohydride (0.52 g, 2.46 mmol) was added slowly and stirred for 3 h at room temperature. Reaction mixture was then poured into water and extracted with $CH_2Cl_2$ (2×20 ml). Combined organic layer was dried over anhyd. $NaSO_4$, and concentrated under vacuum. Crude product was chromatographed over silica gel using benzene-hexane (50:50) as eluant to furnish amino functionalized 1,2,4-trioxane 4eg as an inseparable mixture of diastereomers (0.52 g, 72.2% yield), m.p. 70–72° C.

Example 35

Biphenyl-2-yl-[3-(1-p-Tolyl-Vinyl)-1,2,5-Trioxa-Spiro[5.5]undec-9-yl]-Amine (Compound 4eh and 4ei, Formula 4, Ar=4-Methylphenyl, R=2-Biphenyl)

Acetic acid (1 ml) was added to mixture of trioxane 3e (0.80 g, 2.59 mmol) and 2-aminobiphenyl (0.41 g, 3.24 mmol) in dichloromethane (30 ml). Reaction mixture was stirred at room temp for half an hour. Sodium triacetoxyborohydride (0.82 g, 3.89 mmol) was added slowly and it was stirred for 3 h at room temperature. The reaction mixture was then poured into water and extracted with $CH_2Cl_2$ (2×25 ml). Combined organic layer was dried over anhyd. $Na_2SO_4$, concentrated under vacuum and the crude product was chromatographed over silica gel using benzene-hexane (50:50) as eluant to furnish amino functionalized 1,2,4-trioxane 4eh (upper $R_f$, 0.29 g, 26.60% yield) and 4ei (lower $R_f$, 0.44 g, 40.3% yield) as oil.

Example 36

(4-Fluoro-Phenyl)-[3-(1-p-Tolyl-Vinyl)-1,2,5-Trioxa-Spiro[5.5]undec-9-yl]-Amine (Compound 4el, Formula 4, Ar=4-Methylphenyl, R=4-Fluorophenyl)

Acetic acid 1(ml) was added to mixture of trioxane 3e (0.30 g, 1.04 mmol) and 4-fluoroaniline (0.14 g, 1.25 mmol) in dichloromethane (20 ml). Reaction mixture was stirred at room temp for half an hour. Sodium triacetoxyborohydride (0.33 g, 1.55 mmol) was added slowly and it was stirred for 3 h at room temperature. The reaction mixture was then poured into water and extracted with $CH_2Cl_2$ (2×20 ml). Combined organic layer was dried over anhyd. $Na_2SO_4$, concentrated under vacuum and the crude product was chromatographed over silica gel using benzene-hexane (50:50) as eluant to furnish amino functionalized 1,2,4-trioxane 4el as an inseparable mixture of diastereomers as oil (0.30 g, 75.1% yield).

Example 37

[3-(1-p-Tolyl-Vinyl)-1,2,5-Trioxa-Spiro[5.5]undec-9-yl]-(4-Trifluoromethyl-Phenyl)-Amine (Compound 4eo, Formula 4, Ar=4-Methylphenyl, R=4-Trifluoromethylphenyl)

Acetic acid (1 ml) is added to mixture of trioxane 3e (0.30 g, 1.04 mmol) and 4-trifluoromethyloaniline (0.21 g, 1.30 mmol) in dichloromethane (20 ml). Reaction mixture was stirred at room temp for half an hour. Sodium triacetoxyborohydride (0.33 g, 1.55 mmol) was added slowly and was stirred for 3 h at room temperature. Reaction mixture was then poured into water and extracted with $CH_2Cl_2$ (2×20 ml). Combined organic layer was dried over anhyd. $Na_2SO_4$, concentrated under vacuum. Crude product was chromatographed over silica gel using benzene-hexane (50:50) as eluant to furnish amino functionalized 1,2,4-trioxane 4eo as an inseparable mixture of diastereomers (0.22 g, 48.7% yield), m.p. 104–106° C.

The following amino functionalized 1,2,4-trioxanes 4ag, 4bf, 4bg, 4bh, 4bi, 4cc, 4cd, 4ce, 4cf, 4cg, 4ch, 4cm, 4cn, 4co, 4df, 4dg, 4dh, 4di, 4dj, 4dk, 4dl, 4dn, 4ej, 4ek, 4em and 4en were prepared following the above procedure (Scheme 1, Table 1).

TABLE 1

| S. No. | Amino Functionalized Trioxane | m.p. | % yield |
|---|---|---|---|
| 1. | [3-(1-Phenyl-vinyl)-1,2,5-trioxa-spiro[5.5]undec-9-yl]-(2-trifluoromethyl-phenyl)-amine (compound 4ag, Formula 4, Ar = phenyl, R = 2-trifluoromethylphenyl). | oil | 43.6 |
| 2. | [3-(1-Biphenyl-4-yl-vinyl)-1,2,5-trioxa-spiro[5.5]undec-9-yl]-(4-fluoro-phenyl)-amine (compound 4bf, Formula 4, Ar = 4-biphenyl, R = 4-fluorophenyl). | oil | 78.7 |

TABLE 1-continued

| S. No. | Amino Functionalized Trioxane | m.p. | % yield |
|---|---|---|---|
| 3. | [3-(1-Biphenyl-4-yl-vinyl)-1,2,5-trioxa-spiro[5.5]undec-9-yl]-(2-trifluoromethyl-phenyl)-amine (compound 4bg, Formula 4, Ar = 4-biphenyl, R = 2-trifluoromethylphenyl). | oil | 43.5 |
| 4. | [3-(1-Biphenyl-4-yl-vinyl)-1,2,5-trioxa-spiro[5.5]undec-9-yl]-(3-trifluoromethyl-phenyl)-amine (compound 4bh, Formula 4, Ar = 4-biphenyl, R = 3-trifluoromethylphenyl). | oil | 58.1 |
| 5. | [3-(1-Biphenyl-4-yl-vinyl)-1,2,5-trioxa-spiro[5.5]undec-9-yl]-(4-trifluoromethyl-phenyl)-amine (compound 4bi, Formula 4, Ar = 4-biphenyl, R = 4-trifluoromethylphenyl). | oil | 44.8 |
| 6. | (4-chloro-phenyl-{3-[1-(4-Chloro-phenyl)-vinyl]-1,2,5-trioxa-spiro[5.5]undec-9-yl}-amine (compound 4cc (upper $R_f$), Formula 4, Ar = 4-chlorophenyl, R = 4-chlorophenyl). | 130–132° C. | 26.6 |
| 7. | (4-chloro-phenyl-{3-[1-(4-Chloro-phenyl)-vinyl]-1,2,5-trioxa-spiro[5.5]undec-9-yl}-amine (compound 4cd (lower $R_f$), Formula 4, Ar = 4-chlorophenyl, R = 4-chlorophenyl). | 138–140° C. | 40.3 |
| 8. | {3-[1-(4-Chloro-phenyl)-vinyl]-1,2,5-trioxa-spiro[5.5]undec-9-yl}-(3,5-dichloro-phenyl)-amine (compound 4ce (upper $R_f$), Formula 4, Ar = 4-chlorophenyl, R = 3,5-dichlorophenyl). | oil | 30.9 |
| 9. | {3-[1-(4-Chloro-phenyl)-vinyl]-1,2,5-trioxa-spiro[5.5]undec-9-yl}-(3,5-dichloro-phenyl)-amine (compound 4cf (lower $R_f$), Formula 4, Ar = 4-chlorophenyl, R = 3,5-dichlorophenyl). | oil | 47.4 |
| 10. | N-(4-{3-[1-(4-Chloro-phenyl)-vinyl]-1,2,5-trioxa-spiro[5.5]undec-9-ylamino}-phenyl)-acetamide (compound 4cg, Formula 4, Ar = 4-chlorophenyl, R = 4-acetylaminophenyl). | 88–90° C. | 83.9 |
| 11. | {3-[1-(4-Chloro-phenyl)-vinyl]-1,2,5-trioxa-spiro[5.5]undec-9-yl}-naphthalen-1-yl-amine (compound 4ch, Formula 4, Ar = 4-chlorophenyl, R = 1-naphthyl). | oil | 77.7 |
| 12. | {3-[1-(4-Chloro-phenyl)-vinyl]-1,2,5-trioxa-spiro[5.5]undec-9-yl}-(4-fluoro-phenyl)-amine (compound 4cm, Formula 4, Ar = 4-chlorophenyl, R = 4-fluorophenyl). | oil | 71.2 |
| 13. | {3-[1-(4-Chloro-phenyl)-vinyl]-1,2,5-trioxa-spiro[5.5]undec-9-yl}-(2-trifluoromethyl-phenyl)-amine (compound 4cn, Formula 4, Ar = 4-chlorophenyl, R = 2-trifluoromethylphenyl). | oil | 37.4 |
| 14. | {3-[1-(4-Chloro-phenyl)-vinyl]-1,2,5-trioxa-spiro[5.5]undec-9-yl}-(3-trifluoromethyl-phenyl)-amine (compound 4co, Formula 4, Ar = 4-chlorophenyl, R = 3-trifluoromethylphenyl). | oil | 72.5 |
| 15. | {3-[1-(4-Methoxy-phenyl)-vinyl]-1,2,5-trioxa-spiro[5.5]undec-9-yl}-naphthalen-1-yl-amine (compound 4df, Formula 4, Ar = 4-methoxyphenyl, R = 1-naphthyl). | oil | 73.4 |
| 16. | Biphenyl-2-yl-{3-[1-(4-methoxy-phenyl)-vinyl]-1,2,5-trioxa-spiro[5.5]undec-9-yl}-amine (compound 4dg (upper $R_f$), Formula 4, Ar = 4-methoxyphenyl, R = 2-biphenyl). | oil | 35.4 |
| 17. | Biphenyl-2-yl-{3-[1-(4-methoxy-phenyl)-vinyl]-1,2,5-trioxa-spiro[5.5]undec-9-yl}-amine (compound 4dh (lower $R_f$), Formula 4, Ar = 4-methoxyphenyl, R = 2-biphenyl). | oil | 52.1 |
| 18. | Biphenyl-4-yl-{3-[1-(4-methoxy-phenyl)-vinyl]-1,2,5-trioxa-spiro[5.5]undec-9-yl}-amine (compound 4di, (Formula 4, Ar = 4-methoxyphenyl, R = 4-biphenyl). | 124–126° C. | 58.4 |
| 19. | 9H-Fluoren-3-yl)-{3-[1-(4-methoxy-phenyl)-vinyl]-1,2,5-trioxa-spiro[5.5]undec-9-yl}-amine (compound 4dj, Formula 4, Ar = 4-methoxyphenyl, R = 2-fluorene). | 166–168° C. | 75.7 |
| 20. | (4-Fluoro-phenyl)-{3-[1-(4-methoxy-phenyl)-vinyl]-1,2,5-trioxa-spiro[5.5]undec-9-yl}-amine (compound 4dk, Formula 4, Ar '2 4-methoxyphenyl, R = 4-fluorophenyl). | oil | 60.2 |
| 21. | {3-[1-(4-Methoxy-phenyl)-vinyl]-1,2,5-trioxa-spiro[5.5]undec-9-yl}-(2-trifluoromethyl-phenyl)-amine (compound 4dl, Formula 4, Ar = 4-methoxyphenyl, R = 2-trifluoromethylphenyl). | oil | 36.4 |
| 22. | {3-[1-(4-Methoxy-phenyl)-vinyl]-1,2,5-trioxa-spiro[5.5]undec-9-yl}-(4-trifluoromethyl-phenyl)-amine (compound 4dn, Formula 4, Ar = 4-methoxyphenyl, R = 4-trifluoromethylphenyl). | oil | 40.6 |
| 23. | Biphenyl-4-yl-[3-(1-p-tolyl-vinyl)-1,2,5-trioxa-spiro[5.5]undec-9-yl]-amine (compound 4ej, Formula 4, Ar = 4-methylphenyl, R = 4-biphenyl). | 123–124° C. | 70.5 |
| 24. | (9H-Fluoren-3-yl)-[3-(1-p-tolyl-vinyl)-1,2,5-trioxa-spiro[5.5]undec-9-yl]-amine (compound 4ek, Formula 4, Ar = 4-methylphenyl, R = 2-fluorene). | 152–154° C. | 85.8 |
| 25. | [3-(1-p-Tolyl-vinyl)-1,2,5-trioxa-spiro[5.5]undec-9-yl]-(2-trifluoromethyl-phenyl)-amine (compound 4em, Formula 4, Ar = 4-methylphenyl, R = 2-trifluoromethylphenyl). | oil | 40.8 |
| 26. | [3-(1-p-Tolyl-vinyl)-1,2,5-trioxa-spiro[5.5]undec-9-yl]-(3-trifluoromethyl-phenyl)-amine (compound 4en, Formula 4, Ar = 4-methylphenyl, R = 3-trifluoromethylphenyl). | oil | 65.2 |

Antimalarial Activity

The antimalarial activity of the test compounds was evaluated in rodent using multidrug resistant strain of *Plasmodium yoelii Nigeriensis* in Swiss mice.

General Procedure

Random bred Swiss mice of either sex (20±2 gm) were inoculated intraperitoneally with $1 \times 10^5$ *P. yoelii* (MDR) parasites on day zero. Treatments with test compounds were administered to group of 5 mice each at different dose levels ranging between 12–96 mg/kg/day. Treatment was administered in groundnut oil intramuscularly and orally for 4 consecutive days (day 0–3). Blood smears from experimental mice were observed on day 4 and 7, day 10 and thereafter at regular intervals till day 28 or death of animal. Parasitaemia level on day 4 was compared with vehicle control group and percent suppression of parasitaemia in treated groups was calculated. For determining curative dose of a compound treated mice were observed till day 28. The dose at which no parasitaemia develop during the observation period was reported as curative dose. Antimalarial data is summarized in Table 2.

TABLE 2

ANTIMALARIAL ACTIVITY OF TRIOXANES AGAINST *P. Yoelii* IN MICE.

| Compound | Dose (mg/kg/day) | Route | % Suppression on Day 4[a] | Mice alive on day-28 |
|---|---|---|---|---|
| 3a | 96 | im | 99 | 0/5 |
| 3b | 96 | im | 100 | 1/5 |
| 3c | 96 | oral | 100 | 0/5 |
| 4aa | 96 | oral | 100 | 5/5 |
|  | 96 | im | 71 | 2/5 |
|  | 48 | oral | 100 | 3/5 |
| 4ab | 96 | oral | 100 | 5/5 |
|  | 48 | oral | 100 | 0/5 |
| 4ac | 96 | oral | 100 | 5/5 |
|  | 96 | im | 74 | 0/5 |
|  | 48 | oral | 100 | 5/5 |

TABLE 2-continued

ANTIMALARIAL ACTIVITY OF TRIOXANES AGAINST P. Yoelii IN MICE.

| Compound | Dose (mg/kg/day) | Route | % Suppression on Day 4[a] | Mice alive on day-28 |
|---|---|---|---|---|
|  | 24 | oral | 100 | 4/10 |
|  | 12 | oral | 100 | 0/5 |
| 4ad | 96 | oral | 100 | 5/5 |
|  | 48 | oral | 100 | 5/5 |
|  | 24 | oral | 100 | 6/10 |
|  | 12 | oral | 99 | 0/5 |
| 4ae | 96 | oral | 100 | 5/5 |
| 4ah | 96 | oral | 100 | 5/5 |
|  | 96 | im | 83 | 0/5 |
|  | 48 | oral | 100 | 5/5 |
|  | 24 | oral | 100 | 1/5 |
| 4ba | 96 | oral | 100 | 5/5 |
| 4bg | 96 | oral | 100 | 2/5 |
| 4cb | 48 | oral | 100 | 5/5 |
| 4cc | 48 | oral | 100 | 5/5 |
|  | 24 | oral | 100 | 4/5 |
| 4cd | 48 | oral | 100 | 5/5 |
|  | 24 | oral | 100 | 4/5 |
| 4ce | 48 | oral | 100 | 4/5 |
|  | 24 | oral | 100 | 2/5 |
| 4cf | 48 | oral | 100 | 2/5 |
|  | 24 | oral | 100 | 1/5 |
| 4ch | 96 | oral | 100 | 2/5 |
| 4cj | 48 | oral | 100 | 5/5 |
|  | 24 | oral | 100 | 2/5 |
| 4ck | 96 | oral | 100 | 2/5 |
| 4co | 96 | oral | 100 | 5/5 |
|  | 96 | im | 73 | 0/5 |
|  | 48 | oral | 100 | 5/5 |
|  | 24 | oral | 100 | 3/5 |
| 4da | 96 | oral | 100 | 0/5 |
|  | 96 | im | 81 | 0/5 |
| 4dc | 96 | oral | 100 | 5/5 |
|  | 96 | im | 100 | 4/5 |
|  | 48 | oral | 100 | 5/5 |
|  | 24 | oral | 100 | 4/5 |
| 4dd | 96 | oral | 100 | 4/5 |
| 4df | 96 | oral | 100 | 5/5 |
|  | 48 | oral | 100 | 2/5 |
| 4dg | 48 | oral | 100 | 3/5 |
|  | 24 | oral | 91 | 1/5 |
| 4dh | 48 | oral | 100 | 5/5 |
|  | 24 | oral | 100 | 5/5 |
| 4dm | 96 | oral | 100 | 5/5 |
|  | 96 | im | 100 | 0/5 |
|  | 48 | oral | 100 | 5/5 |
|  | 24 | oral | 100 | 5/5 |
| 4ea | 96 | oral | 100 | 5/5 |
|  | 96 | im | 96 | 0/5 |
| 4eb | 96 | oral | 100 | 5/5 |
|  | 96 | im | 93 | 0/5 |
| 4ec | 96 | oral | 100 | 5/5 |
| 4ed | 48 | oral | 100 | 4/5 |
|  | 24 | oral | 95 | 0/5 |
| 4ee | 48 | oral | 100 | 2/5 |
|  | 24 | oral | 81 | 0/5 |
| 4eg | 96 | oral | 100 | 5/5 |
| 4ej | 96 | oral | 100 | 5/5 |
|  | 96 | im | 69 | 0/5 |
|  | 48 | oral | 100 | 2/5 |
| 4en | 96 | oral | 100 | 3/5 |
| β-Arteether | 48 | oral | 100 | 5/5 |
|  | 24 | oral | 100 | 1/5 |
| Chloroquine | 48 | oral | 100 | 2/5 |
|  | 24 | oral | 100 | 0/5 |
| Vehicle Control | — | — | — | 0/15 |

[a]Percent suppression = $[(C - T)/C] \times 100$; where C = parasitaemia in control group, and T = parasitaemia in treated group.

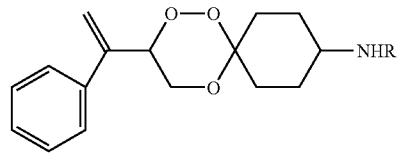

4aa–4ai

4aa  R = 4-chlorophenyl
4ab  R = 2-biphenyl (upper $R_f$)
4ac  R = 2-biphenyl (lower $R_f$)
4ad  R = 4-biphenyl
4ae  R = 2-fluorene
4af  R = 4-fluorophenyl
4ag  R = 2-trifluoromethylphenyl
4ah  R = 3-trifluoromethylphenyl
4ai  R = 4-trifluoromethylphenyl

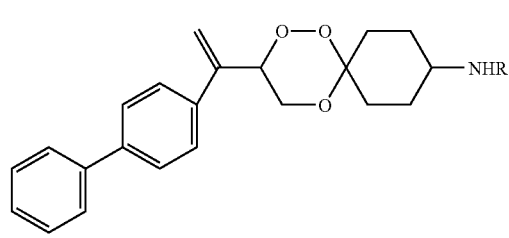

4ba–4bi

4ba  R = 4-chlorophenyl
4bb  R = 2-biphenyl (upper $R_f$)
4bc  R = 2-biphenyl (lower $R_f$)
4bd  R = 4-biphenyl
4be  R = 2-fluorene
4bf  R = 4-fluorophenyl
4bg  R = 2-trifluoromethylphenyl
4bh  R = 3-trifluoromethylphenyl
4bi  R = 4-trifluoromethylphenyl

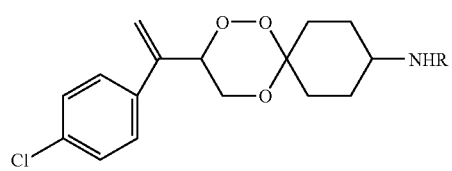

4ca–4cp

4ca  R = phenyl
4cb  R = 4-methoxyphenyl
4cc  R = 4-chlorophenyl (upper $R_f$)
4cd  R = 4-chlorophenyl (lower $R_f$)
4ce  R = 3,5-dichlorophenyl (upper $R_f$)
4cf  R = 3,5-dichlorophenyl (lower $R_f$)
4cg  R = 4-acetylaminophenyl
4ch  R = 1-naphthyl
4ci  R = 2-biphenyl (upper $R_f$)
4cj  R = 2-biphenyl (lower $R_f$)
4ck  R = 4-biphenyl
4cl  R = 2-fluorene
4cm  R = 2-fluorophenyl
4cn  R = 2-trifluoromethylphenyl
4co  R = 3-trifluoromethylphenyl
4cp  R = 4-trifluoromethylphenyl -continued

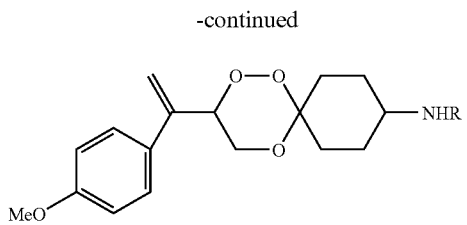

4da–4dn

4da  R = phenyl
4db  R = 4-methoxyphenyl
4dc  R = 4-chlorophenyl
4dd  R = 3,5-dichlorophenyl
4de  R = 4-acetylaminophenyl
4df  R = 1-naphthyl
4dg  R = 2-biphenyl (upper $R_f$)
4dh  R = 2-biphenyl (lower $R_f$)
4di  R = 4-biphenyl
4dj  R = 2-fluorene
4dk  R = 2-fluorophenyl
4dl  R = 2-trifluoromethylphenyl
4dm  R = 3-trifluoromethylphenyl
4dn  R = 4-trifluoromethylphenyl

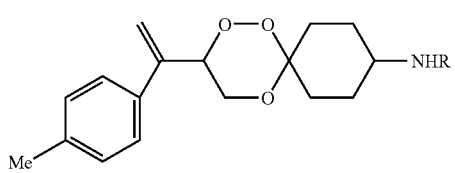

4ea–4eo

4ea  R = phenyl
4eb  R = 4-methoxyphenyl
4ec  R = 4-chlorophenyl
4ed  R = 3,5-dichlorophenyl (upper $R_f$)
4ee  R = 3,5-dichlorophenyl (lower $R_f$)
4ef  R = 4-acetylaminophenyl
4eg  R = 1-naphthyl
4eh  R = 2-biphenyl (upper $R_f$)
4ei  R = 2-biphenyl (lower $R_f$)
4ej  R = 4-biphenyl
4ek  R = 2-fluorene
4el  R = 2-fluorophenyl
4em  R = 2-trifluoromethylphenyl
4en  R = 3-trifluoromethylphenyl
4eo  R = 4-trifluoromethylphenyl

We claim:

1. A substituted amino functionalized 1,2,4-trioxane of formula 4

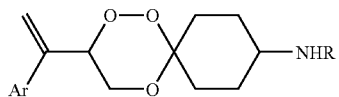

4 wherein Ar represents aryl groups selected from the groups consisting of phenyl, 4-biphenyl, 4-chlorophenyl, 4-methoxyphenyl and 4-methylphenyl and R represents phenyl, 4-methoxyphenyl, 4-chlorophenyl, 3,5-dichlorophenyl, 4-acetylaminophenyl, 1-naphthyl, 2-biphenyl, 4-biphenyl, 2-fluorene, 4-fluorophenyl, 2-trifluoromethylphenyl, 3-trifluoromethylphenyl and 4-trifluoromethylphenyl.

2. Compound of formula 4 with structural formula 4aa–4ai shown below:

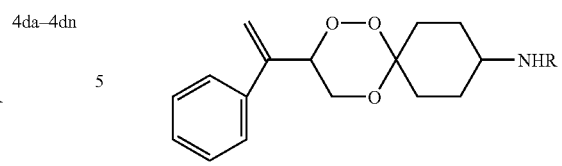

4aa–4ai

4aa  R = 4-chlorophenyl
4ab  R = 2-biphenyl (upper $R_f$)
4ac  R = 2-biphenyl (lower $R_f$)
4ad  R = 4-biphenyl
4ae  R = 2-fluorene
4af  R = 4-fluorophenyl
4ag  R = 2-trifluoromethylphenyl
4ah  R = 3-trifluoromethylphenyl
4ai  R = 4-trifluoromethylphenyl.

3. Compound of formula 4 with structural formula 4ba–4bi shown below:

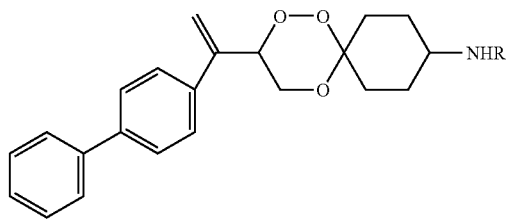

4ba–4bi

4ba  R = 4-chlorophenyl
4bb  R = 2-biphenyl (upper $R_f$)
4bc  R = 2-biphenyl (lower $R_f$)
4bd  R = 4-biphenyl
4be  R = 2-fluorene
4bf  R = 4-fluorophenyl
4bg  R = 2-trifluoromethylphenyl
4bh  R = 3-trifluoromethylphenyl
4bi  R = 4-trifluoromethylphenyl.

4. Compound of formula 4 with structural formula 4ca–4cp shown below:

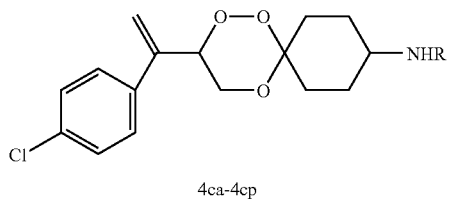

4ca–4cp

4ca  R = phenyl
4cb  R = 4-methoxyphenyl
4cc  R = 4-chlorophenyl (upper $R_f$)
4cd  R = 4-chlorophenyl (lower $R_f$)
4ce  R = 3,5-dichlorophenyl (upper $R_f$)
4cf  R = 3,5-dichlorophenyl (lower $R_f$)
4cg  R = 4-acetylaminophenyl
4ch  R = 1-naphthyl
4ci  R = 2-biphenyl (upper $R_f$)
4cj  R = 2-biphenyl (lower $R_f$)
4ck  R = 4-biphenyl
4cl  R = 2-fluorene
4cm  R = 4-fluorophenyl
4cn  R = 2-trifluoromethylphenyl
4co  R = 3-trifluoromethylphenyl
4cp  R = 4-trifluoromethylphenyl.

5. Compound of formula 4 with structural formula 4da–4dn shown below:

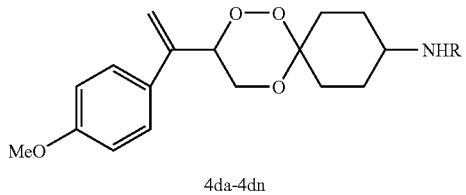

4da–4dn

4da R = phenyl
4db R = 4-methoxyphenyl
4dc R = 4-chlorophenyl
4dd R = 3,5-dichlorophenyl
4de R = 4-acetylaminophenyl
4df R = 1-naphthyl
4dg R = 2-biphenyl (upper $R_f$)
4dh R = 2-biphenyl (lower $R_f$)
4di R = 4-biphenyl
4dj R = 2-fluorene
4dk R = 4-fluorophenyl
4dl R = 2-trifluoromethylphenyl
4dm R = 3-trifluoromethylphenyl
4dn R = 4-trifluoromethylphenyl.

6. Compound of formula 4 with structural formula 4ea–4eo shown below:

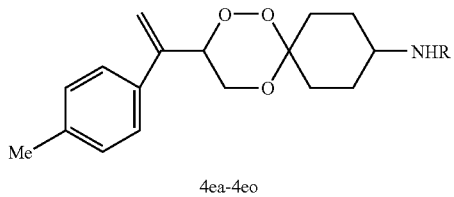

4ea–4eo

4ea R = phenyl
4eb R = 4-methoxyphenyl
4cc R = 4-chlorophenyl
4ed R = 3,5-dichlorophenyl (upper $R_f$)
4ee R = 3,5-dichlorophenyl (lower $R_f$)
4ef R = 4-acetylaminophenyl
4eg R = 1-naphthyl
4eh R = 2-biphenyl (upper $R_f$)
4ei R = 2-biphenyl (lower $R_f$)
4ej R = 4-biphenyl
4ek R = 2-fluorene
4el R = 4-fluorophenyl
4em R = 2-trifluoromethylphenyl
4en R = 3-trifluoromethylphenyl
4eo R = 4-trifluoromethylphenyl.

7. Method for the preparation of a substituted amino functionalized-1,2,4-trioxane of formula 4

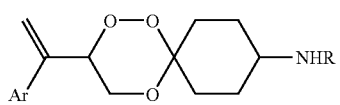

4 wherein Ar represents aryl groups selected from the groups consisting of phenyl, 4-biphenyl, 4-chlorophenyl, 4-methoxyphenyl and 4-methylphenyl and R represents phenyl, 4-methoxyphenyl, 4-chlorophenyl, 3,5-dichlorophenyl, 4-acetylaminophenyl, 1-naphthyl, 2-biphenyl, 4-biphenyl, 2-fluorene, 4-fluorophenyl, 2-trifluoromethylphenyl, 3-trifluoromethylphenyl and 4-trifluoromethylphenyl, the process comprising reacting a keto trioxane of formula 3

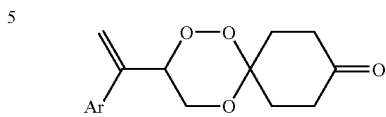

3 with an aromatic amine in the presence of $NaBH(OAc)_3$ in $CH_2Cl_2$ to furnish amino functionalized 1,2,4-trioxanes of formula 4.

8. A method as claimed in claim 7 wherein the aromatic amine is selected from the group consisting of aniline, 4-methoxyaniline, 4-chloroaniline, 3,5-dichloroaniline, 4-aminoacetanilide, 1-naphthylamine, 2-aminobiphenyl, 4-aminobiphenyl, 2-aminofluorene, 4-fluoroaniline, 2-trifluoromethylaniline, 3-trifluoromethylaniline and 4-trifluoromethylaniline.

9. A method for the preparation of substituted amino functionalized-1,2,4-trioxanes of formula 4

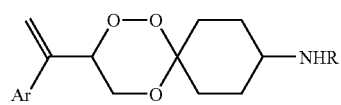

4 wherein Ar is an aryl group selected from the group consisting of phenyl, 4-biphenyl, 4-chlorophenyl, 4-methoxyphenyl and 4-methylphenyl and R represents phenyl, 4-methoxyphenyl, 4-chlorophenyl, 3,5-dichlorophenyl, 4-acetylaminophenyl, 1-naphthyl, 2-biphenyl, 4-biphenyl, 2-fluorene, 4-fluorophenyl, 2-trifluoromethylphenyl, 3-trifluoromethylphenyl and 4-trifluoromethylphenyl, the method comprising:

(i) photooxygenating an allylic alcohol of formula 1 by passing oxygen gas or air in a solution of the alcohol in an organic solvent and in the presence of a dye and a light source which provides visible light, for a period of 4 h, to obtain a β-hydrohydroperoxide of formula 2

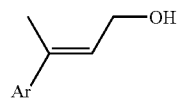

1

1a; Ar = Phenyl
1b; Ar = 4-Biphenyl
1c; Ar = 4-chlorophenyl
1d; Ar = 4-methoxyphenyl
1e; Ar = 4-methylphenyl

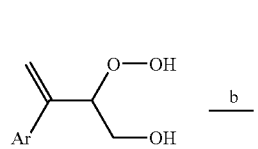

2

2a; Ar = Phenyl
2b; Ar = 4-Biphenyl
2c; Ar = 4- chlorophenyl
2d; Ar = 4- methoxyphenyl
2e; Ar = 4- methylphenyl (ii) reacting the hydroperixodes of formula 2 in situ with 1,4-cyclohexanedione in the presence of an acid catalyst to give a trioxane of formula 3;

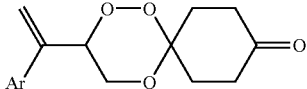

3

3a; Ar = Phenyl
3b; Ar = 4-Biphenyl
3c; Ar = 4-chlorophenyl
3d; Ar = 4-methoxyphenyl
3e; Ar = 4-methylphenyl reacting the keto trioxane of formula 3 with an aromatic amine in the presence of NaBH(OAc)$_3$ in CH$_2$Cl$_2$ to obtain amino functionalized 1,2,4-trioxane of formula 4.

10. A method as claimed in claim 9 wherein the aromatic amine is selected from the group consisting of aniline, 4-methoxyaniline, 4-chloroaniline, 3,5-dichloroaniline, 4-aminoacetanilide, 1-naphthylamine, 2-aminobiphenyl, 4-aminobiphenyl, 2-aminofluorene, 4-fluoroaniline, 2-trifluoromethylaniline, 3-trifluoromethylaniline and 4-trifluoromethylaniline.

11. A method of treating a subject having malaria, comprising administering to the subject a pharmaceutically effective amount of a composition containing substituted amino functionalized-1,2,4-trioxanes of formula 4,

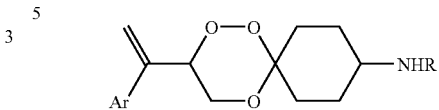

4 wherein Ar represents aryl groups selected from the groups consisting of phenyl, 4-biphenyl, 4-chlorophenyl, 4-methoxyphenyl and 4-methylphenyl and R represents phenyl, 4-methoxyphenyl, 4-chlorophenyl, 3,5-dichlorophenyl, 4-acetylaminophenyl, 1-naphthyl, 2-biphenyl, 4-biphenyl, 2-fluorene, 4-fluorophenyl, 2-trifluoromethylphenyl, 3-trifluoromethylphenyl and 4-trifluoromethylphenyl and a pharmaceutically acceptable carrier.

12. A method as claimed in claim 11 wherein the composition is administered intramuscularly or orally.

13. A method as claimed in claim 11 wherein the pharmaceutically acceptable amount of compound of formula 4 is in the range of 12 to 96 mg of compound of formula 4 per kilogram of body weight of subject per day.

14. A method as claimed in claim 11 wherein the subject is a human being.

* * * * *

UNITED STATES PATENT AND TRADEMARK OFFICE
CERTIFICATE OF CORRECTION

| | | |
|---|---|---|
| PATENT NO. | : 7,071,226 B1 | Page 1 of 1 |
| APPLICATION NO. | : 11/023905 | |
| DATED | : July 4, 2006 | |
| INVENTOR(S) | : Chandan Singh et al. | |

It is certified that error appears in the above-identified patent and that said Letters Patent is hereby corrected as shown below:

Title Page, Item (75) Inventors should read:

-Chandan Singh-
    -Heetika Malik-
    -Sunil Kumar Puri-

Signed and Sealed this

Twenty-first Day of November, 2006

JON W. DUDAS
*Director of the United States Patent and Trademark Office*